US011083759B2

(12) United States Patent
Han

(10) Patent No.: US 11,083,759 B2
(45) Date of Patent: Aug. 10, 2021

(54) ORAL MICROBIOTA TRANSFORMATION FOR THE RELIEF OF IMMUNE SYSTEM ASSOCIATED INFLAMMATIONS

(71) Applicant: Knoze Jr. Corporation, Los Alamos, NM (US)

(72) Inventor: Shunsheng Han, Los Alamos, NM (US)

(73) Assignee: Knoze Jr. Corporation, Los Alamos, NM (US)

( * ) Notice: Subject to any disclaimer, the term of this patent is extended or adjusted under 35 U.S.C. 154(b) by 55 days.

(21) Appl. No.: 16/505,341

(22) Filed: Jul. 8, 2019

(65) Prior Publication Data

US 2019/0343899 A1    Nov. 14, 2019

Related U.S. Application Data

(63) Continuation-in-part of application No. 16/001,808, filed on Jun. 6, 2018, now Pat. No. 10,471,033, which is a continuation-in-part of application No. 15/706,323, filed on Sep. 15, 2017, now Pat. No. 10,398,670.

(51) Int. Cl.
| | |
|---|---|
| *A61K 35/744* | (2015.01) |
| *A61K 31/198* | (2006.01) |
| *A61K 9/00* | (2006.01) |
| *A61K 47/36* | (2006.01) |
| *A61K 47/26* | (2006.01) |

(52) U.S. Cl.
CPC .......... *A61K 35/744* (2013.01); *A61K 9/0053* (2013.01); *A61K 31/198* (2013.01); *A61K 47/26* (2013.01); *A61K 47/36* (2013.01)

(58) Field of Classification Search
CPC ..... A61K 35/744; A61K 9/0053; A61K 47/36
See application file for complete search history.

(56) References Cited

U.S. PATENT DOCUMENTS

2017/0071986 A1* 3/2017 Kovarik .................. A61K 31/65

FOREIGN PATENT DOCUMENTS

WO    WO-2017129050 A1 *  8/2017  ........... A61K 31/715

OTHER PUBLICATIONS

Kolderman et al. "L-Arginine Destabilizes Oral Multi-Species Biofilm Communities Developed in Human Saliva" (PLoS One 2015, 10(5): 60121835, pp. 1-18) (Year: 2015).*
Koopman et al. "Changes in the oral ecosystem induced by the use of 8% arginine toothpaste" (Archives of Oral Biology 73 (2017) 79-87) (Year: 2017).*
Cosseau, C. et al. "The Commensal *Streptococcus salivarius* K12 Downregulates the Innate Immune Responses of Human Epithelial Cells and Promotes Host-Microbe Homeostasis" Infection and Immunity, Sep. 2008, 4163-4175 (Year: 2008).*
Zhang, R. et al. "L-Arginine administration attenuates airway inflammation by altering L-arginine metabolism in an NC/Nga mouse model of asthma" J. Clin. Biochem. Nutr., May 2015, 56, 3, 201-207 (Year: 2015).*
Mashima, I. et al. "Identification of *Veillonella* Species in the Tongue Biofilm by Using a Novel One-Step Polymerase Chain Reaction Method" PLoS One 2016, 11(6): e0157516, pp. 1-16 (Year: 2016).*
Lucotti, P. et al. "Oral L-arginine supplementation improves endothelial function and ameliorates insulin sensitivity and inflammation in cardiopathic nondiabetic patients after an aortocoronary bypass" Metabolism Clinical and Experimental 58 (2009) 1270-1276 (Year: 2009).*
VanHoute, J. et al. "Relationship Between the Concentration of Bacteria in Saliva and the Colonization of Teeth in Humans" Infection and Immunity, Apr. 1974, 624-630 (Year: 1974).*
Machine translation of WO-2017129050-A1, 2020, pp. 1-13 (Year: 2020).*

* cited by examiner

*Primary Examiner* — Andrew S Rosenthal
(74) *Attorney, Agent, or Firm* — Caldwell Intellectual Property Law, LLC

(57)    ABSTRACT

A method of selectively promoting a desired oral microbiota to treat an inflammation condition associated with an allergic reaction in a subject in need of such treatment including providing a composition including: at least one live bacterial population including lactic acid producing bacteria and lactic acid fermenting bacteria; and, an amino acid containing ingredient comprising L-arginine; at least partially removing a biofilm within an oral cavity of the subject; wherein the composition is contained within the oral cavity of the subject in an effective amount to selectively promote an increased concentration of selected oral microbiota comprising the lactic acid producing bacteria and the lactic acid fermenting bacteria to thereby treat the inflammation condition.

19 Claims, No Drawings

ORAL MICROBIOTA TRANSFORMATION FOR THE RELIEF OF IMMUNE SYSTEM ASSOCIATED INFLAMMATIONS

The disclosure generally relates to compositions and methods for treating immune system modulated Inflammations including the addition of selected live microbial populations to a microbiome including *Veillonella* and *Streptococcus* to aid in the selective altering of bacterial populations in a microbiome to thereby promote healthy operation of the immune system.

More particularly, the disclosure relates to compositions and methods for treating Immune System modulated Inflammations which may include partial or substantial removal of oral biofilms including the addition of selected live microbial populations to an oral cavity including *Veillonella* and *Streptococcus* to achieve the targeted modulation of microbial populations including the oral microbiota. The selected altering of the oral microbiota may thereby promote the naturally occurring healthy operation of the immune system including reducing respiratory allergic reactions (including allergic reactions to self-antigens that lead to autoimmune diseases) as well as other oral and/or sinus infections and/or inflammations.

BACKGROUND

In general, the prevalence of allergic diseases has dramatically increased in recent decades and currently affects more than sixty million people in the United States, reducing the quality of life. It is believed and has been found that the presence of certain oral bacteria species/strains may affect the aggressiveness of response of the immune system including with respect to allergic reactions as well as contributing to other oral and/or sinus infections. More specifically, while not intending to be bound by any health claims, it is believed that the reduction of normally occurring (commensal) oral bacteria in the normally occurring oral microbiota, for example, by aggressive dental hygiene practices, may serve to make non-pathogenic antigens, such as pollen, more prevalent and visible to the immune system. It is further believed, that as a result, non-pathogenic antigens may be more readily targeted by the immune system, leading to exacerbated allergic reactions and/or inflammations (including allergic reactions to self-antigens that lead to autoimmune diseases) as well as other oral and/or breathing passage associated infections and/or inflammations.

For example, oral hygiene hypothesis (OHH) is one aspect of a more general hygiene hypothesis (HH), which was proposed more than two decades ago (see Strachan, D. P. "Hay fever, hygiene, and household size", British Medical Journal 299, 1259-1260 (1989)) to explain the rise in allergic diseases. Numerous scientific studies have since provided support for HH, generally showing a relation between increased exhibition of allergies in association with modern social practices, such as formula infant feeding, antibiotic use, urban living, and reduction in family size (see e.g., Okada, H., Kuhn, C., Feillet, H. & Bach, J. F., "The hygiene hypothesis for autoimmune and allergic diseases: an update" Clin. Exp. Immunol. 160, 1-9 (2010)). Although the molecular mechanisms of immune system modulation by gut microbiota are well understood, efforts to reduce allergic reactions through microbial intervention, such as by the use of probiotics have shown inconsistent results.

Extensive oral hygiene practices, according to oral hygiene hypothesis (Han, C S., "A specific hygiene hypothesis" Med. Hypotheses 2016 August 93:146-149), are believed to cause the exacerbation of naturally occurring respiratory allergies, such as allergic rhinitis (AR), one of the most common allergic conditions.

Conversely, not intending to be bound by theory and health claims, it is believed that an over-abundance of certain normally occurring (commensal) oral bacteria in the normally occurring oral microbiota, for example, leading to a de-sensitized or abnormally functioning immune system may cause normally non-pathogenic normally occurring oral bacteria to become pathogenic, resulting in chronic attack and resulting inflammation by the immune system thereby resulting in chronic pathogenic conditions related to several types of oral and/or breathing passage related inflammations, infections and/or obstructions associated with exacerbated allergic reactions and/or inflammations.

There is therefore a need for an oral microbiota promoting composition that selectively promotes a desired oral microbiota and method of using the same that has the effect of promoting the healthy operation of the immune system and which may have the functional effect of promoting an improved response to allergens as well as reducing associated allergic reactions and/or inflammations (including allergic reactions to self-antigens that lead to autoimmune diseases) as well as other oral and/or breathing passage associated infections and/or inflammations.

It is an object of the invention to provide an oral microbiota promoting composition and that selectively promotes a desired oral microbiota and method of using the same that has the effect of promoting the healthy operation of the immune system and which may have the functional effect of promoting an improved response to allergens as well as reducing associated allergic reactions and/or inflammations (including allergic reactions to self-antigens that lead to autoimmune diseases) as well as other oral and/or breathing passage associated infections and/or inflammations.

SUMMARY

A method of selectively promoting a desired oral microbiota to treat an inflammation condition associated with an allergic reaction in a subject in need of such treatment including providing a composition including: at least one live bacterial population including lactic acid producing bacteria and lactic acid fermenting bacteria; and, an amino acid containing ingredient comprising L-arginine; at least partially removing a biofilm included within an oral cavity of the subject; wherein the composition is contained within the oral cavity of the subject in an effective amount to selectively promote an increased concentration of selected oral microbiota comprising the lactic acid producing bacteria and the lactic acid fermenting bacteria to thereby treat the inflammation condition.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. The use of the term "about" is generally meant to include values within 1% of the cited value unless another meaning is indicated. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

It is believed, and has been found that according to the oral hygiene hypothesis (OHH) noted above, that persistent and intensive hygiene practices, together with other life events, such as fever and/or antibiotic usage, will likely change the oral microbiota of an individual. The oral cavity is a complex environment with many different surfaces as biological niches, such as the tongue, gums, teeth and other oral cavity surfaces. Normally occurring microbiota associated with these niches are different and are believed to have a different effect on normal functioning of the immune system.

Likewise, the introduction of selected live bacterial populations optionally together with and/or subsequent addition of substances into the oral cavity in a controlled manner that may promote the selected live bacterial populations as well as naturally occurring oral bacteria species/strains which may be the same or different than the selected live bacterial populations.

In addition, the decrease of targeted bacterial populations including naturally occurring and/or selectively introduced live bacterial populations may be achieved by exposing the targeted bacteria to a substance which decreases the targeted bacteria population. Selective control of the relative populations of selected bacteria populations may in turn have an associated effect of modulating the intensity of oral and/or sinus inflammations, and/or allergic reactions, and/or pulmonary inflammations.

While not intending to be bound by any particular theory of operation, and making no specific health claims, it is believed that oral microbiota interact with the host largely through metabolites produced by its relevant bacterial members. Those metabolites, such as but not limited to short chain fatty acid, may influence the function of multiple biologic systems and organs, such as the immune system. Missing or severe reduction of the relevant naturally occurring beneficial (commensal) bacteria may cause malfunctioning of the immune system, such as causing over-sensitivity to commensal bacteria and/or allergens (including self-antigens). Commensal microflora (normal microflora, indigenous microbiota) consists of those micro-organisms, which are present on body surfaces covered by epithelial cells and are exposed to the external environment (gastro-intestinal and respiratory tract, vagina, skin, etc.).

It is known that in both autoimmune and allergic diseases, the condition arises through aberrant responses of the human immune system to antigens including self-antigens (originating from within the body). In autoimmunity, the patient's immune system is activated against the body's own proteins by a response to self-antigens, while in allergies, against external antigens-allergens.

Under specific conditions, the commensal bacteria that produce substances that pacify (calm down) the immune system may become insufficient and without enough of a pacifying effect, causing the immune system to become hypersensitive and exert pathologic effects. Therefore, in certain embodiments the immune system response to the allergens (including self-antigens) and/or commensal bacteria may be modulated by the method and/or composition such that the associated oral and/or breathing passage inflammations and/or allergic reaction symptoms are suppressed relative to what an infection and/or allergic reaction may be with an unhealthy level of commensal microbiota.

As a result of promoting a healthy oral microbiota with added live microbial populations and optional selected microbiota-promoting substances, the immune system may function in a healthy manner with a health promoting response to allergens, (including self-antigens), and/or commensal bacteria that have become pathogenic.

Furthermore, due to the connectivity among mouth and respiratory duct and lungs, a healthy oral microbiota may lead to a healthy microbiota in the lungs as well. Eventually the method and/or composition may benefit the healthy functioning of the immune system which may in turn have a healthy response not only to oral and/or breathing passage inflammations related to an allergic response but also relevant inflammations in the lungs, such as pulmonary obstructions.

For example, in other embodiments, the method and/or composition may benefit the healthy functioning of the immune system with respect to oral and/or sinus inflammations as well as infections including breathing passage related inflammations including but not limited to inflammations having symptoms related to, or similar to, gingivitis, periodontitis (periodontal disease), tonsillitis, rhinosinusitis, pharyngitis, laryngitis, and pulmonary obstructions. While some or a portion of these inflammations may be caused by pathogen invasion, an overly sensitized immune system attacking commensal bacteria may lead to the exacerbation and/or cause of inflammations associated with other opportunistic (pathenogenic) commensal bacteria caused infections.

In other embodiments, the method and/or composition may benefit the healthy functioning of the immune system with respect to inflammatory conditions having symptoms similar to or related to autoimmune reactions locally in the neck/head area or in other parts of the body, such as but not limited to alopecia, arthritis, systemic lupus and erythematosus.

In an under-sensitized immune system some or a portion of these inflammations may be caused by commensal bacteria becoming pathogenic (opportunistic) resulting in chronic attack by the immune system leading to the exacerbation and/or cause of inflammations including those associated with oral cavity and/or breathing passage related inflammations.

The method and/or composition may be used to promote a healthy functioning of an immune system e.g., by reducing immune system sensitivity in an over-sensitized immune system or increasing immune system sensitivity in an under-sensitized immune system by restoring a healthy level of desired commensal bacteria to thereby at least reduce or alleviate symptoms associated with immune system promoting inflammatory conditions including oral and/or breathing passage related inflammations, infections, obstructions, and/or allergens.

In one embodiment, live oral bacterial populations including at least one population of lactic acid producing bacteria may be included in an oral microbiome promoting composition and introduced into the oral cavity.

In another embodiment, live oral bacterial populations including at least one population of lactic acid consuming (fermenting) bacteria may be included in the oral microbiome promoting composition and introduced into the oral cavity.

In another embodiment the lactic acid producing and/or the lactic acid fermenting (fermenting) bacteria may produce short chain fatty acids.

In one embodiment, the lactic acid producing population may comprise one or more desired microbial members such as *Streptococcus* including one or more associated species, such as, but not limited to, *(S.) salivarius (S.) australis, S. gordonii* and *(S.) thermophilus*.

In another embodiment the lactic acid consuming (fermenting) bacteria may comprise one or more desired microbial members such as *Veillonella* including associated species, such as, but not limited to, *Veillonella* species such as *(V.) Dispar* and *(V.) Parvula*.

In a related embodiment, the desired live microbial species/strains may be provided within the oral cavity at a concentration of from about 1000 to about 1,000,000,000 living cells, more preferably from about 5000 to about 500,000,000 living cells even more preferably from about 10,000 to about 250,000,000 living cells.

In a related embodiment, the desired live microbial species/strains may be provided separately or included within a carrier such as a powder and/or liquid or with the oral microbiota promoting composition.

It will be appreciated that the desired live microbial species/strains may be obtained commercially and should be handled in accordance with any applicable safety requirements.

In another embodiment, the desired microbial species/strains promoted in the oral cavity by the oral microbiota promoting composition may include at least a first microbial species that can attach to surfaces (e.g., teeth, tongue, mouth) within the oral cavity and at least one second microbial species that may attach to the same or different surfaces and/or may attach to the at least first microbial species.

In a related embodiment, the at least a first and second microbial species may produce a product, such as a sugar containing moiety, that may be metabolized by the other of the at least a first and second microbial species.

In another embodiment, an oral microbiota promoting composition may not include live bacterial populations which may be provided separately and/or may be naturally occurring within an oral cavity and that may have the effect of promoting the desired microbiota, including before, after, or together with introduction of live bacterial populations to achieve the desired microbiota within the oral cavity.

In other embodiments, the selected live bacterial populations may be provided separately or included in an oral microbiota promoting composition.

In another embodiment, a method of applying the selected live bacterial populations and/or an oral microbiota promoting composition (prebiotic) may have the effect of promoting desired microbiota including one or more of *Veillonella* and *Streptococcus* within an oral cavity which may be included in the live bacterial populations and/or may be already present as naturally occurring microbiota within the oral cavity and which may have the desired functional effect of promoting a healthy response to oral cavity and/or sinus inflammations including breathing passage inflammations and/or pulmonary obstructions related to allergic reactions.

In one embodiment, promoting desired microbiota within an oral cavity may be accomplished by promoting an increase in the relative concentration of selected bacterial species such as *Veillonella* and *Streptococcus*. For example the desired selected bacterial species may be increased to a relative concentration (relative to all other types of bacterial species percent within the oral cavity) of from about 5% to about 30%, more preferably, from about 6% to about 20%, even more preferably from about 8% to about 12% of the relative types of bacterial present within a sampled area of the oral cavity.

In some embodiments, the relative percentage of the desired bacterial species population within the oral cavity may be determined by one or more of weight, volume, and/or individual bacterium counting methods and be primarily with respect to substantially similar comparative samples taken from one or more of saliva, tongue, throat, and inside surfaces of the oral cavity including dental portions.

In another embodiment, promoting desired microbiota within an oral cavity may be accomplished by promoting a decrease in the relative concentration of selected bacterial species. For example the desired selected bacterial species may be decreased to a relative concentration (relative to all types of bacterial species present from a sampled area within the oral cavity) of from about 5% to about 30%, more preferably, from about 6% to about 20%, even more preferably from about 8% to about 12%.

In one embodiment, promoting desired microbiota within an oral cavity may be accomplished by exposing the microbiota within an oral cavity to an oral microbiota promoting composition that promotes the growth of targeted bacteria that comprises the desired microbiota.

In another embodiment, promoting desired microbiota within an oral cavity may be accomplished by exposing the microbiota within an oral cavity to a substance that inhibits in some degree, the growth of targeted bacteria that comprises the desired microbiota.

In one embodiment, the targeted bacterial species may comprise one or more desired microbial members such as *Veillonella* including associated species, such as, but not limited to, *Veillonella* species such as *(V.) Dispar* and *(V.) Parvula* and *Streptococcus* species including one or more associated species, such as, but not limited to, *(S.) salivarius (S.) australis, S. gordonii* and *(S.) thermophilus*.

In another embodiment, the targeted bacterial species may comprise a species other than the one or more desired microbial members that may have the effect of crowding out or replacing the population of beneficial bacterial species and thereby reducing the relative concentration (relative with respect to a selected one and/or all other bacterial species present) of targeted bacterial populations that have reached an undesireably high relative concentration.

For example in one embodiment if it is determined that one or more of the desired bacterial species including *Veillonella* species such as *(V.) Dispar* and *(V). Parvula*, and *Streptococcus* species such as *(S.) australis, S. gordonii* and *S. salivarius* have reached an undesirably high concentration e.g., from about 70 percent to about 100 percent (with respect to all bacterial species present), then a competing bacterial species, such as *S. mitis* and *S. dentisani*, and the like, may be selectively promoted in order to compete with and thereby reduce (crowd out) concentrations of the overly-concentrated bacterial populations.

For example, in one embodiment, competing bacterial species may be promoted by changing the composition of an oral microbiota promoting composition including the presence of live bacterial populations, e.g., an oral microbiota promoting composition that includes live bacterial populations and/or has the effect of promoting already present desired *Veillonella* and/or *Streptococcus* species may be made less promoting to the desired bacterial species and/or more promoting to a competing bacterial species by leaving out one or more ingredients in an oral microbiota promoting compositions (including live bacterial populations), such as one or more sugars, such as one or more monosaccharides and/or disaccharides, and/or adding alternative oral microbiota promoting ingredients (including live bacterial populations such as *S. mitis* and *S. dentisani*) and/or nutrients such as raffinose, which may be preferred by *S. mitis*.

Alternatively or additionally, an undesirably high population of normally beneficial species such as *Veillonella* or *Streptococcus* may be reduced and re-established at a lower relative concentration level (relative to a selected one or more bacterial populations present in the oral cavity) by partially or substantially removing a biofilm within the oral cavity and together with or followed by introducing live bacterial populations and/or applying an oral microbiota promoting composition as outlined below.

For example, partially or substantially removing a biofilm within the oral cavity and/or applying the live bacterial and/or oral microbiota promoting composition may have the beneficial effect of resetting or adjusting selected oral microbiota concentrations including desired relative concentrations of the desired bacterial species such as *Veillonella* and/or *Streptococcus* as previously discussed.

For example, in one embodiment, the relative desired level of desired bacterial species in a stable steady state within the oral cavity may be from about 30 percent to about 80 percent (e.g., based on a counting percentage of a selected bacterial species with respect to all bacterial species present from a sample area within the oral cavity), more preferably from about 35 percent to about 70 percent, even more preferably from about 40 percent to about 60 percent.

In one embodiment, a method of applying an oral microbiota promoting composition (which may include live bacterial populations) may include multiple instances of introduction of the composition (together or separately from live bacterial populations) into the oral cavity (mouth) in the form of a solid, powder, paste, or liquid in the amount of about 1 gm to about 500 gms at one time or multiple times in fractional amounts. Where the oral microbiota promoting composition is in the form of liquid, the method may include first dissolving the composition in a liquid.

In another embodiment, a method of applying an oral microbiota promoting composition may include swallowing the composition following introduction of the composition into the oral cavity and following a period of retaining the composition within the mouth for a select period of time including e.g., chewing, gargling, and/or sublimating (dissolving) the composition while within the oral cavity.

In another embodiment, a method of applying an oral microbiota promoting composition may include removing the composition following introduction into the oral cavity by expelling (e.g., pulling out or spitting-out) the microbiota promoting composition following a period of retaining the composition within the mouth.

In another embodiment, a method of applying an oral microbiota promoting composition may include retaining the microbiota promoting composition within the oral cavity from about 10 seconds to about an hour, more preferably, from about 5 minutes to about 30 minutes on a daily basis for a period of about 2 days to about 60 days.

In another embodiment, a method of applying an oral microbiota promoting composition may include introducing the microbiota promoting composition for relatively short periods several times a day, for example from about 1 second to about 30 seconds, each from about 3 to about 10 times a day for a period of about 2 days to about 60 days.

In another embodiment, a method of applying an oral microbiota promoting composition may include extending the periods of introduction of the microbiota promoting composition into the oral cavity, for example, from about every 3 days to about every 10 days, including stopping the introduction of the composition following the disappearance of symptoms related to a treatment condition.

In another embodiment, a method of applying an oral microbiota promoting composition may include at least partially, including substantially, removing a mucosal film (biofilm) from surfaces within the oral cavity prior to or while administering the microbiota promoting composition to the oral cavity.

By the term partially removing is meant is meant removal of from about 20% to about 70% of a biofilm as determined by sampling saliva and/or representative surfaces defining major surface areas (e.g. samples from one or more of the tongue, mouth, throat, and teeth) within the oral cavity, e.g., removing from about 20% to about 70% of a biofilm from representative areas (e.g., greater than about 90%) of the sampled surface areas supporting the biofilm within the oral cavity.

By the term substantially removing is meant removal of from about greater that 70% to about 100% of a biofilm as determined by sampling saliva and/or representative surfaces defining major surface areas (e.g. samples from one or more of the tongue, mouth, throat, and teeth) within the oral cavity, e.g., removing from about 70% to about 100% of a biofilm from representative areas (e.g., greater than about 90%) of the sampled representative surface areas supporting the biofilm within the oral cavity.

Biofilms are defined as living bacterial populations adherent to each other and/or to surfaces including within porous surfaces and which populations live within a matrix of cells and extracellular polymers including those produced by the bacterial populations. A biofilm possesses a natural resistance to surfactants and other chemicals and provides protection from antibacterial agents which may be effective against free-floating or planktonic bacteria outside the biofilm.

In one embodiment, a biofilm with the oral cavity may be partially or substantially removed by exposing the biofilm to one or more biofilm degrading enzymes in an effective amount to accomplish such removal. The effective amount may be effective in disrupting the matrix of extracellular polymers. By disrupting is meant chemically changing the matrix of extracellular polymers sufficient to allow chemical penetration of the matrix by the one or more enzymes and/or other chemicals or antibacterial agents.

It is well known in the art that the matrix of extracellular polymers includes polysaccharides (exopolysaccharides) that function as a backbone of the biofilm and include one or more of glucose, galactose, mannose, fructose, rhamnose, ribose, glucosamine, galactosamine, mannuronic acid, galacturonic acid and glucuronic acid (see I. W. Sutherland in "Surface Carbohydrates of the Procaryotic Cell", 27-96, Academic Press, London, 1977, which is hereby incorporated by reference).

In one embodiment, the one or more biofilm degrading enzymes may include deglycosylate biopolymers such as glycoproteins. For example, the enzyme may include one or more endoglycosidases.

It will be appreciated that known methods including methods using r-DNA together with selected bacterial strains to produce and isolate enzymes are known in the art and may be used to produce the one or more biofilm degrading enzymes.

In another embodiment the one or more biofilm degrading enzymes may be included in a mixture of enzymes including one or more of alpha-amylase, a protease and a cellulase (see U.S. Pat. No. 5,071,765, which is hereby incorporated by reference).

In another embodiment, the one or more biofilm degrading enzymes may be included in a mixture of enzymes including one or more of galactosidase, galacturonidase, rhamnosidase, xylosidase, fucosidase, arabinosidase and alpha-glucosidase (see U.S. Pat. No. 5,238,572, which is hereby incorporated by reference).

In another embodiment the one or more biofilm degrading enzymes may be included in a mixture of enzymes including one or more of polysaccharidases, proteases, lipases and glycoproteases (see EP0820516B1, which is hereby incorporated by reference).

In another embodiment the one or more biofilm degrading enzymes may include glycosidases.

In another embodiment the one or more biofilm degrading enzymes may include DNase I of bacterial origin or DNase enzymes isolated from other organisms including humans (see US Patent US20130052250A1 which is incorporated herein by reference).

In another embodiment the one or more biofilm degrading enzymes may be include polysaccharide hydrolases such as Glucan hydrolases including one or more of mutanases and dextranases (see Pleszczyńska, M. Wiater, A. Bachanek, T. Szczodrak J., "Enzymatic removal and disinfection of bacterial biofilms", Biotechnology and Applied Biochemistry, 2017, which is hereby incorporated by reference).

In one embodiment the one or more biofilm degrading enzymes may include a polysaccharide-degrading enzyme.

In another embodiment the one or more biofilm degrading enzymes may include one or more hydrolytic enzymes capable of degrading an exopolysaccharide backbone structure of a biofilm which may include alginates formed by bacteria within the biofilm (see U.S. Pat. No. 6,830,745B1, which is hereby incorporated by reference).

In another embodiment the one or more biofilm degrading enzymes may include one or more hydrolytic enzymes capable of degrading proteins, polypeptides, and lipids, such as lipopolysaccharides and lipoproteins comprising the biofilm.

In another embodiment, the one or more biofilm degrading enzymes may include one or more chemical moieties attached to the one or more enzymes that have the capability of binding to the biofilm, e.g., either through hydrogen bonding such as with amine or carboxylate containing moieties or covalently such as through nitrogen-nitrogen, nitrogen-carbon or carbon-carbon bonding.

In another embodiment, the one or more biofilm degrading enzymes may include a functional ability to generate an active oxygen species including oxido-reductases.

In another embodiment, the one or more biofilm degrading enzymes may include polysaccharide lyases.

In one embodiment, the one or more biofilm degrading enzymes may include lyases capable of lysing alginate, such as alginates forming a portion of the biofilm (see which is hereby incorporated by reference).

In another embodiment, non-enzymatic bactericidal components such as antimicrobial agents, antibiotics, and sanitizing agents may be provided with or separately from the one or more enzymes.

For example, the one or more biofilm degrading enzymes and/or non-enzymatic bactericidal components may be provided into the oral cavity by a carrier including a solid or liquid carrier such as a solution, spray, tablet, or emulsion, and/or released into the oral cavity by being provided in a carrier or supported on a bio-adhesive support using similar methods further discussed below for delivering a preferred microbiota promoting composition. In some embodiments the biofilm degrading enzymes may be delivered with or separately from the preferred microbiota promoting composition.

In one embodiment the biofilm may be at least partially removed (e.g., from about 20% to about 70%), or substantially removed (e.g., from greater than about 70% to about 100% (e.g., by weight, volume, bacterium counting, and/or surface area of the biofilm), by a process which includes raising the whole body temperature, or at least the oral cavity temperature to a temperature from about 90 to about 130 degrees Fahrenheit for a short time period, e.g., from about 1 minute to about 1 hour, for example, with conventional biological or physical means.

In another embodiment, the biofilm may be partially or substantially removed by exposing the biofilm to one or more biofilm degrading enzymes together with substantially simultaneously or subsequently raising the temperature within the oral cavity. The methods of heating the oral cavity and/or exposure to biofilm degrading enzymes may be performed substantially simultaneously or sequentially in any order.

In one embodiment, the one or more biofilm degrading enzymes may be provided within the oral cavity to initially disrupt the biofilm, followed by heating the oral cavity.

In another embodiment, the oral cavity may be first heated, followed by the use of the one or more biofilm degrading enzymes, including optionally heating the oral cavity subsequent to the use of the one or more biofilm degrading enzymes.

In another embodiment, rubbing or scrubbing the inside of the oral cavity may be performed substantially simultaneously or sequentially to steps including one or more of heating and/or exposing the oral cavity to one or more biofilm degrading enzymes to at least partially, including substantially, remove the biofilm.

For example, the use of one or more biofilm degrading enzymes may be provided prior to or substantially simultaneously with rubbing and/or brushing the inside of the oral cavity, followed by heating the inside of the oral cavity with a heated liquid with optional additional rubbing and/or brushing to at least partially and/or substantially remove the biofilm.

It will be appreciated that the rubbing or brushing may be performed by any conventional method including with one or more of a brush, such as a toothbrush, a scrapper and/or a wet cloth, which may optionally include the prior, simultaneous or subsequent use of sonic energy applied to the rubbed or brushed area of the oral cavity.

In a related embodiment, the biofilm may be at least partially and/or substantially removed where heating the inside of the oral cavity may include rinsing of the oral cavity (mouth) with a heated liquid, such as a water-containing liquid (optionally including prior, simultaneous, and/or subsequent brushing or rubbing).

In some embodiment, the temperature of the heated liquid may be from about 80 to about 130 degrees Fahrenheit, more preferably from about 90 to about 120 degrees Fahrenheit, even more preferably from about 105 to about 120 degrees Fahrenheit.

In some embodiments, the oral rinsing may include periodic rinsing, for example, multiple periods where each period is preformed for about 10 seconds to about 30 seconds over a period of from about 5 to about 15 minutes.

In some embodiments the removal of the biofilm within the oral cavity may take place prior to and/or substantially simultaneous with the application of a microbiota promoting composition and/or live bacterial populations within the oral cavity. It will be appreciated that the live bacterial populations are preferably introduced following removal of the biofilm, but may be introduced without removing the biofilm.

It will be appreciated that at least partially removing, including substantially removing a biofilm from surfaces within the oral cavity, for example, biofilms on the dental surfaces and tongue, has been found to improve the promotion of desired selected bacteria to achieve a desired oral microbiome by the use of the oral microbiota promoting composition and/or live bacterial populations.

In another embodiment, the oral microbiota promoting composition and/or live bacterial populations may be formulated into oral dosage forms such as tablets, caplets, and capsules, or a powder formulation or that may be dissolved in a liquid, for example diluted in a liquid having a ratio of from about 1:1 to about 1:500 with respect to either weight or volume of the liquid (e.g., the liquid being larger number).

In another embodiment, the oral microbiota promoting composition (optionally including live bacterial populations) may be formulated or manufactured as soft candy and/or may include edible food gelling agents such as starch, vegetable pectin, and/or gelatin such as, corn starch, potato starch, carrageenan, and/or any other gelatin.

The addition of gelling agents preferably enables the microbiota promoting composition to be dissolved and released into the oral cavity over an extended period of time.

The gelling agents may be present at a ratio of from about 1:10 to about 1:100 with respect to either weight or volume of the microbiota promoting composition.

For example, in some preferred embodiments, the microbiota promoting composition is formed as a solid and/or gel that may be dissolved relatively slowly over a period of time within the oral cavity to release ingredients that may promote the desired microbiota within the oral cavity over a selected period of time.

It has been found and is expected that the promotion of the desired concentrations of desired microbiota such as *Veillonella* and *Streptococcus* are promoted more effectively to desired concentrations with the oral cavity by a relatively slow release of ingredients within the microbiota promoting composition.

In one embodiment, the microbiota promoting composition may be formed as a solid, gel and/or include gel forming ingredients, so that the ingredients included in a selected dose, capsule or tablet are released from about 50% to about 100% over a period of from about 1 minute to about 60 minutes while being maintained within the oral cavity.

In one embodiment the microbiota promoting composition may be formed as a layered solid, gel and/or gel forming ingredients including layers of different relative concentrations of the microbiota promoting compositional ingredients.

In one embodiment, at least one of one or more of live bacterial ingredients and/or free amino acids may be included with higher relative concentrations in outermost layers, with underlying layers having higher relative concentrations of sugars and other ingredients providing nutrition to the desired microbiota population.

In another embodiment, the oral microbiota promoting composition (optionally including live bacterial populations) may be formulated as an additive to an oral hygiene product acting as a carrier, such as toothpaste or mouthwash, the microbiota promoting composition having a ratio of from about 1:1 to about 1:500 with respect to either weight or volume of the oral hygiene product.

In another embodiment, the oral microbiota promoting composition (optionally including live bacterial populations) may be provided on bioadhesive delivery devices such as bioadhesive strips that are known in the art. For example, the composition may be provided on or infused into a bioadhesive strip, such as on a bioadhesive or self-adhesive support which supports the composition. For example, the composition may be included in a gel, such as a carbohydrate based gel that may be supported on a solid support, such as a plastic or cross-linked polymer support that may include micro-patterns on a supporting surface (e.g., having spacings of about 0.1 to about 2 mm). The bioadhesive strip infused with or supporting the oral microbiota promoting composition may be self-adhesive (in the presence of oral saliva) to dental or mucosal portions of the oral cavity.

In a related embodiment, the one or more biofilm degrading enzymes may be provided within the bioadhesive delivery device, and formulated to be released into the oral cavity prior to and/or substantially simultaneous with the release of the oral microbiota promoting composition. For example, the one or more enzymes and the oral microbiota promoting composition may be formulated for controlled time-release for example by mixing with or encapsulating within time-release dissolving substances that are known in the art.

Where live bacterial populations are applied, it may be preferable to add any live bacterial populations following biofilm removal steps, if any, to avoid adversely affecting the live bacterial populations.

In another embodiment, the oral microbiota promoting composition (which may include live bacterial populations) may be formulated having an edible foodstuff as a carrier, the microbiota promoting composition having a ratio of from about 1:1 to about 1:500 with respect to either weight or volume of the edible foodstuff.

In one embodiment, the desired microbial species/strains promoted in the oral cavity by the oral microbiota promoting composition may be naturally occurring within the oral cavity and/or may be provided or supplemented with live bacterial populations including within the oral microbiota promoting composition.

In another embodiment, an oral microbiota promoting composition is provided that includes at least one amino acid and/or amino acid containing substance including substantially individual separate molecules (free amino acid) of the amino acid. By the term substantially individual separate molecules of the amino acid means greater than about 80% to about 99% of a particular amino acid is present as individual separate molecules (free amino acid). For example, it has been found that individual molecules of amino acids (as opposed to amino acid chains) are more readily metabolized and have the desired effect of promoting the selected bacterial populations.

In one embodiment the oral microbiota promoting composition includes L-arginine. The at least one amino acid may further or alternately include at least one of L-cysteine, DL-aspartic acid, L-glutamic acid, L-serine and L-tyrosine including phosphates, salts, acids, and enzymes comprising the same.

In preferred embodiments, the at least one amino acid may be introduced into the composition including substantially individual molecules of a respective amino acid, including at least L-arginine. In another embodiment, the at least one amino acid may be substantially decomposed into individual molecules of the amino acid following introduction into the oral cavity.

In another embodiment, the at least one amino acid including at least L-arginine, is configured to be present substantially as individual molecules (also referred to as free arginine) with the oral cavity, e.g., dissolve and/or decompose and or be solvated as individual molecules of L-arginine.

For example, it is believed, and has been observed that L-arginine residues in long or short peptide chains may not accomplish the desired promotion of the desired microbiota within the oral cavity, including with the desired health promoting effect, including the promotion of desired *Veillonella* and *Streptococcus* species as previously discussed.

In some embodiments, the L-arginine may be present as substantially individual molecules (also referred to as free arginine) present in associated salts and/or acids such as but not limited to, L-arginine HCl (Hydrogen Chloride), Arginine mononitrate, and L-arginine glutamate.

In a related embodiment, the at least one amino acid, may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In some embodiments, such as in the example recipe given below, the at least one amino acid, may be present in the oral microbiota promoting composition at a weight percent level of from about 2.0 wt. % to about 10 wt %, and in some preferred embodiments from about 2.5 wt % to about 10 wt. %

In another embodiment, an oral microbiota promoting composition may include at least one sugar containing substance and at least one amino acid containing substance. The at least one sugar containing substance may include at least one monosaccharide, disaccharide, oligosaccharide, and polysaccharide.

In some embodiments, the oral microbiota promoting composition may be limited to L-arginine as the amino acid containing substance and the sugars may be limited to one or more monosaccharides and disaccharides.

Exemplary monosaccharides may include but are not limited to aldohexoses such as but not limited to mannose including associated isomers, phosphates, salts, acids, and enzymes comprising the same.

Exemplary disaccharides may include but are not limited to disaccharides including at least one of galactose and glucose, such as but not limited to lactose, sucrose, malibiose, maltose, cellobiose and trehalose (also known as mycose or tremalose) including associated isomers, phosphates, salts, acids, and enzymes comprising the same.

Exemplary oligosaccharides may include but are not limited to trisaccharides including at least one or more of galactose, glucose, and fructose, such as but not limited to raffinose (also known as melitose), stachyose, and verbascose, including associated isomers, phosphates, salts, acids, and enzymes comprising the same.

Further, Exemplary polysaccharides may include but are not limited to one or more polysaccharide polymers, such as, but not limited to polysaccharides including malotriose units, including but not limited to pullulan, and fructose polymers, such as, but not limited to inulin and further including associated isomers, phosphates, salts, acids, and enzymes comprising the same.

In a related embodiment, the at least one disaccharide may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In a related embodiment, the at least one oligosaccharide may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In a related embodiment, the at least one polysaccharide may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In another embodiment, the oral microbiota promoting composition may include at least one prebiotic fiber. Exemplary prebiotic fibers may include but are not limited to inulin.

In a related embodiment, the at least one prebiotic fiber may be present in the oral microbiota promoting composition at a weight percent level of from about 0.1 wt. % to about 99.9 wt. %, more preferably, from about 5 wt % to about 95 wt %, even more preferably from about 10 wt % to 30 wt %.

In another embodiment the oral microbiota promoting composition may include additives such as one or more of carbohydrates, amino acids, salts, flavorants, proteins, surfactants, emulsifiers, flavonoids, alcohols, synthetic sweeteners, food preserving agents, and combinations thereof.

In one embodiment, the oral microbiota promoting composition may further include conventional foodstuffs such as one or more of brown sugar, a sugar containing syrup, honey, chocolate, nuts, almonds, spices, cinnamon, and vanilla.

In another embodiment, the oral microbiota promoting composition may further include extract from fruits, such as jujube fruit extract which may include one or more of rhamnose, xylitol, arabitol, fructose, glucose, inositol, sucrose, and maltose.

In a specific exemplary embodiment, an example of making an edible Foodstuff oral microbiota promoting composition is provided below in Example 1:

Example 1

1 cup raffinose
1 cup trehalose
2 tablespoons mannose
1 cup lactose
½ cup maltose
½ cup L-arginine
2 tablespoons pullulan
1 cup inulin
1 cup dark brown sugar
½ cup corn syrup
½ cup honey
1 cup milk chocolate
1 cup chocolate chips
¼ cup toasted almonds (small chips)
¼ cup carrageenan
¼ tablespoon cinnamon
¼ tablespoon vanilla extract In one embodiment, the above ingredients may be admixed and heated to a temperature sufficient to melt or liquefy, preferably avoiding boiling for an extended period and then poured into a container to cool.

In another embodiment, live bacterial populations, such as those previously outlined, may be provided in accordance with safety requirements or limitations.

In one embodiment, the selected live bacterial populations may be added following cooling (e.g., as a coating). It will be appreciated that adding the bacterium may be limited by applicable safety precautions and may reduce the shelf life of the product.

It will be appreciated that in other embodiments, the live bacterial populations may be added to oral cavity separately (before or after) exposing the oral cavity to the oral microbiota promoting composition (which may or may not include the live bacterial populations).

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of selectively promoting a desired oral microbiota to treat an inflammation condition associated with an allergic reaction in a subject in need of such treatment comprising: providing a composition comprising: at least one live bacterial population comprising lactic acid producing bacteria and lactic acid fermenting bacteria; a sugar, wherein the sugar comprises at least one polysaccharide, and wherein the at least one polysaccharide comprises one or more of pullulan and inulin; and an amino acid containing ingredient comprising L-arginine; at least partially removing a biofilm within an oral cavity of the subject; wherein the composition is contained within the oral cavity of the subject in an effective amount to selectively promote an increased concentration of selected oral microbiota comprising the lactic acid producing bacteria and the lactic acid fermenting bacteria to thereby treat the inflammation condition.

2. The method of claim 1, wherein the lactic acid producing bacteria comprise *Streptococcus* and the lactic acid fermenting bacteria comprise *Veillonella*.

3. The method of claim 2, wherein *Streptococcus* includes one or more of *S. salivarius* and *S. thermophilus* and wherein *Veillonella* comprises one or more of *V. dispar* and *V. parvula*.

4. The method of claim 1, wherein the lactic acid producing bacteria and a lactic acid fermenting bacterium are each at a concentration of from about 1000 to about 1,000,000,000 living cells.

5. The method of claim 1, wherein the inflammation condition comprises one or more of gingivitis, periodontitis, tonsillitis, rhinosinusitis, pharyngitis, and laryngitis.

6. The method of claim 1, wherein the inflammation condition comprises one or more of lupus, arthritis and autoimmune diseases having the inflammation condition present on one or more of the head, neck and lungs.

7. The method of claim 1, wherein removing the biofilm comprises exposing the biofilm to at least one biofilm degrading enzyme.

8. The method of claim 1, wherein removing a biofilm comprises heating portions of the oral cavity including one or more major surface areas of the oral cavity to a temperature of from about 90 deg F. to about 130 deg F.

9. The method of claim 1, wherein removing a biofilm comprises at least one of brushing and rubbing surfaces within the oral cavity.

10. The method of claim 1, wherein the L-arginine is configured to be present as separate individual molecules of L-arginine within an oral cavity of the subject.

11. The method of claim 10, wherein the L-arginine comprises one or more salts of L-arginine including one or more of L-arginine HCl, and L-arginine glutamate.

12. The method of claim 1, wherein the amino acid containing ingredient further comprises at least one of L-cysteine, DL-aspartic acid, L-glutamic acid, L-serine, and L-tyrosine.

13. The method of claim 1, wherein the composition is provided within the oral cavity by at least one of being provided in a carrier and supported on a support surface.

14. The method of claim 1, wherein the composition is provided within the oral cavity for a period of at least from about 30 seconds to about an hour on a daily basis comprising at least one day.

15. The method of claim 1, wherein the sugar further comprises one or more of mannose, lactose, melibiose, maltose, cellobiose, trehalose, raffinose, stachyose, and verbascose.

16. The method of claim 1, wherein the sugar further comprises at least one of jujube fruit extract and one or more of rhamnose, xylitol, arabitol, fructose, glucose, inositol, sucrose, and maltose.

17. The method of claim 1, wherein the selected microbiota are selectively promoted to the increased concentration within the oral cavity of about 35 percent to about 70 percent with respect to all bacterial species present within the oral cavity.

18. A formulated oral prebiotic composition useful for promoting a desired oral microbiota to treat an inflammation condition associated with an allergic reaction in a subject in need of such treatment, the composition comprising: at least one live bacterial population comprising lactic acid producing bacteria and lactic acid fermenting bacteria; a sugar, wherein the sugar comprises at least one polysaccharide, and wherein the at least one polysaccharide comprises one or more of pullulan and inulin, and an amino acid containing ingredient comprising L-arginine; wherein the composition is in a configuration suitable to be maintained including being dissolved within the oral cavity over a period of at least about 1 minute to about an hour in an effective amount to thereby selectively promote an increased concentration of selected oral microbiota to thereby treat the allergy related respiratory condition, the selected oral microbiota comprising *Veillonella* and *Streptococcus*.

19. The method of claim 1, wherein the at least one polysaccharide is present at a weight percent level from about 5 weight percent to about 95 weight percent.

* * * * *